US00PP16029P2

(12) United States Plant Patent
Whetman

(10) Patent No.: US PP16,029 P2
(45) Date of Patent: Oct. 11, 2005

(54) ***DIANTHUS* PLANT NAMED 'DEVON YOLANDE'**

(50) Latin Name: *Dianthus×hybrida*
Varietal Denomination: Devon Yolande

(76) Inventor: John Whetman, Deer Park Farm, Chudleigh, Devon TQ13 ONH (GB)

( * ) Notice: Subject to any disclaimer, the term of this patent is extended or adjusted under 35 U.S.C. 154(b) by 248 days.

(21) Appl. No.: 10/805,444

(22) Filed: Mar. 22, 2004

(51) Int. Cl.[7] ..... A01H 5/00
(52) U.S. Cl. ..... Plt./273
(58) Field of Search ..... Plt./273

*Primary Examiner*—Anne Marie Grunberg
*Assistant Examiner*—June Hwu

(57) ABSTRACT

A new cultivar of *Dianthus* plant named 'Devon Yolande' that is characterized by compact mounding habit, grayish blue-green foliage and fragrant pink flowers with red-purple markings. In combination these traits set 'Devon Yolande' apart from all other existing varieties of *Dianthus* known to the inventor.

2 Drawing Sheets

Genus: *Dianthus.*
Species: *×hybrida.*
Denomination: Devon Yolande.

BACKGROUND OF THE INVENTION

The present invention relates to a new and distinct cultivar of *Dianthus*, or garden pink, that is grown for use as an ornamental landscape and container plant. It is known botanically as *Dianthus×hybrida* and will be referred to hereinafter by the cultivar name 'Devon Yolande'.

'Devon Yolande' is the product of a breeding program started by the inventor in 1980 in a cultivated area of Houndspool, Dawlish, Devon, United Kingdom. The primary focus of the breeding program is to produce new cultivars of garden pinks that exhibit unique characteristics of flower color and form, and which, preferably, are highly and pleasantly fragrant. In addition, new varieties are selected for being well-proportioned in respect of ratio of overall height (including flower canopy) to overall width.

Ordinarily, the inventor carries out controlled crosses, with known parents, and selects new varieties for sets of similar characteristics in order to make whole sets of series. 'Devon Yolande' is a chance hybrid plant that was selected in 2000 as a single seedling from a large group (which the inventor designated as Family 9722) of open-pollinated seedlings which itself had resulted from open-pollination of a group of unnamed and unreleased plants of *Dianthus* from the inventor's large collection of *Dianthus*. Thus, on this occasion, the inventor is unable to identify either the male or the female parent, or to draw comparisons between 'Devon Yolande' and either parent.

However, 'Devon Yolande' may be compared with the Inventor's variety of *Dianthus* named 'Devon PP11', U.S. Plant Pat. No. 14,919. Whereas each flower stem of 'Devon PP 11' generally bears one single flower or bud, the flower stems of 'Devon Yolande' typically carry from two to five flowers and buds. The overall effect of a mature plant of 'Devon Yolande' is to display a dense mound of flowers and buds.

'Devon Yolande' was selected for its distinguishing combination of compact well-proportioned habit, floriferous blooming, perfume fragrance and double bi-colored flowers. The inventor is not aware of any plant in commerce which is close to 'Devon Yolande' in bearing such a combination of characteristics.

Asexual reproduction of the new cultivar was first accomplished by the inventor in 2000, in a cultivated area of Houndspool, United Kingdom. The method of asexual propagation used was stem cuttings, Since that time the characteristics of the new cultivar have been determined stable and are reproduced true to type in successive generations by vegetative propagation.

SUMMARY OF THE INVENTION

The following traits have been repeatedly observed and represent the characteristics of the new *Dianthus* cultivar, 'Devon Yolande'. These traits in combination distinguish this cultivar from all other commercial varieties known to the inventor. 'Devon Yolande' has not been tested under all possible conditions and phenotypic differences may be observed with variations in environmental, climatic and cultural conditions without however any difference in genotype.

1. *Dianthus* 'Devon Yolande' exhibits a compact mounding growth habit.
2. *Dianthus* 'Devon Yolande' exhibits grayish blue-green foliage.
3. *Dianthus* 'Devon Yolande' exhibits fragrant pink flowers with red-purple markings.
4. *Dianthus* 'Devon Yolande' is 18–25 cm. in overall height, including flower canopy, and 20–25 cm in width in a 1.5-liter container.
5. *Dianthus* 'Devon Yolande' is an evergreen perennial ornamental.
6. *Dianthus* 'Devon Yolande' blooms from May to October.
7. *Dianthus* 'Devon Yolande' is hardy to minus 15° Centigrade.

BRIEF DESCRIPTION OF THE DRAWINGS

The accompanying color drawings illustrate the overall appearance of the new *Dianthus* variety 'Devon Yolande' showing colors as true as it is reasonably possible to obtain in colored reproductions of this type. Colors in the drawings may differ from the color values cited in the detailed botanical description, which accurately describe the actual colors of the new variety 'Devon Yolande'.

The drawing labeled as FIG. 1 illustrates the entire plant in flower.

Figure 1:
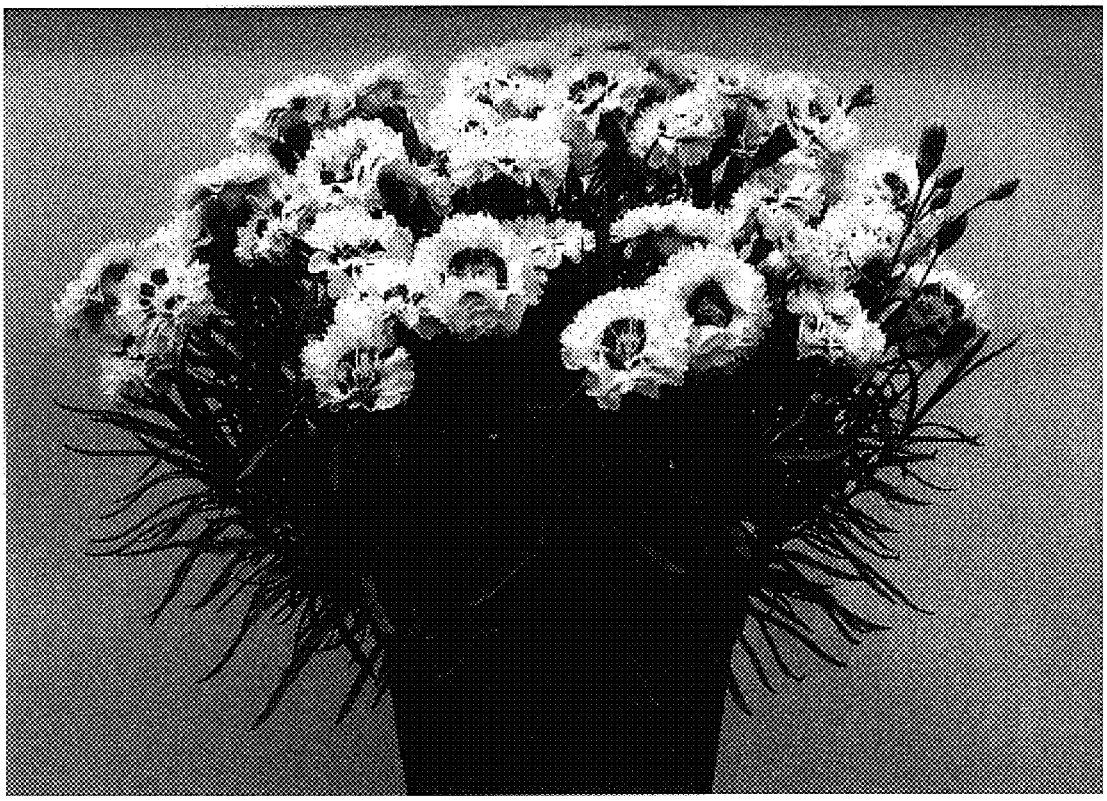
Figure 2:
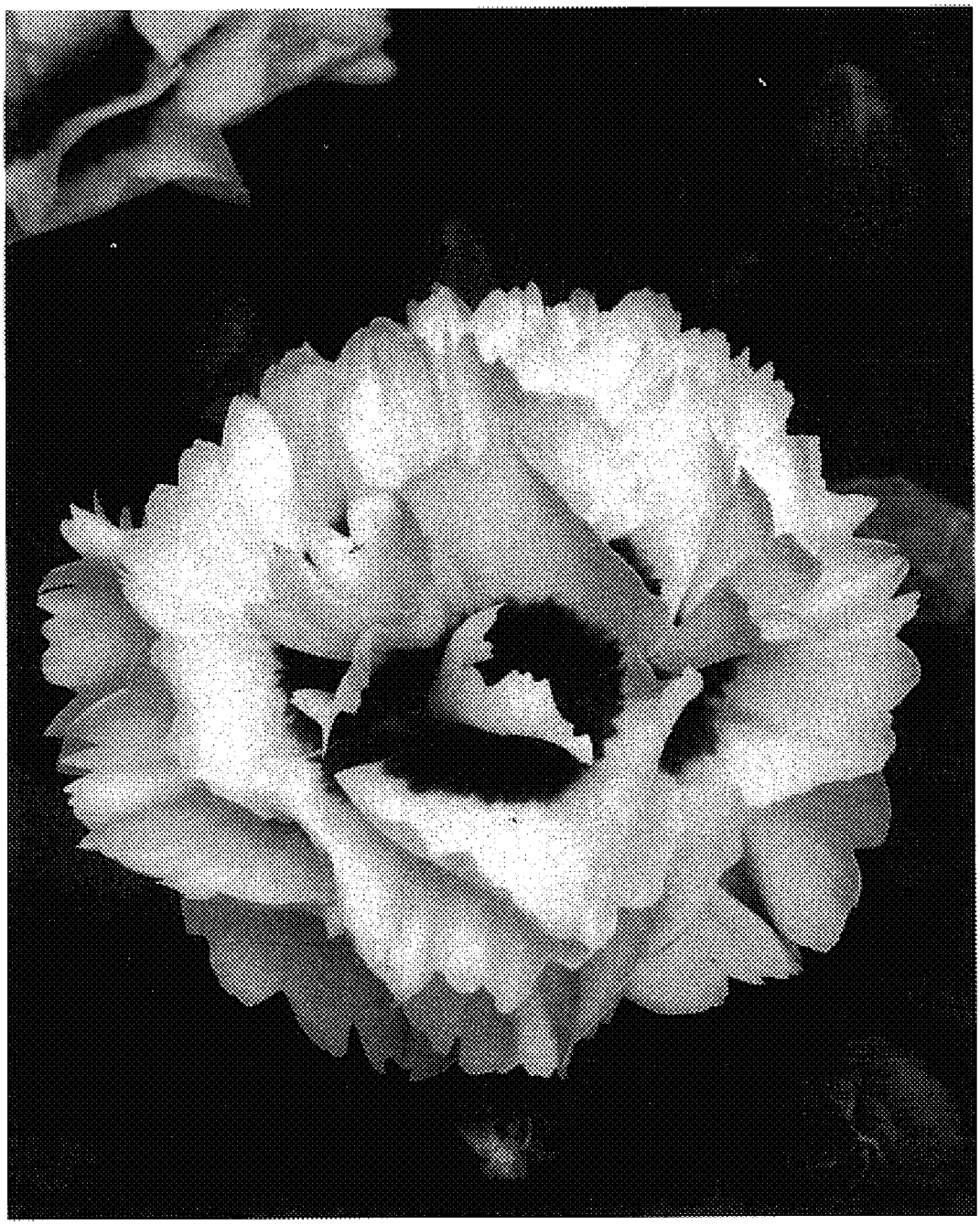

The drawing labeled as FIG. 2 is a close-up of a typical flower.

All drawings were made of plants grown in 1.5-liter containers under a cold glasshouse in Houndspool, Devon, United Kingdom. No chemicals were used to treat the plants. All drawings were made using conventional techniques and although colors may appear different from actual colors due to light reflectance they are as accurate as possible by conventional photography.

BOTANICAL DESCRIPTION OF THE PLANT

The following is a detailed description of the new cultivar 'Devon Yolande'. Data was collected from plants grown in 1.5-liter containers under a cold glasshouse in Houndspool, United Kingdom. The color determinations are in accordance with the 2002 edition of The Royal Horticultural Society Colour Chart of The Royal Horticultural Society, London, England, except where general color terms of ordinary dictionary significance are used. No chemicals were used to treat the plants. Growing conditions are typical to other *Dianthus*.

Botanical classification: *Dianthus* 'Devon Yolande'.
Species: ×*hybrida*.
Common name: Hybrid *dianthus*.
Commercial classification: Hardy perennial herb.
Use: Ornamental plant for small pots and containers.
Parentage: 'Devon Yolande' is a hybrid plant that resulted from the open pollination of a group of unidentified *Dianthus* seedlings.
- *Female parent plant.*—Unidentified individual *Dianthus* plant.
- *Male parent plant.*—Unidentified individual *Dianthus* plant.

Plant description:
- *Bloom period.*—May to October.
- *Plant habit.*—Compact mounding habit.
- *Plant height.*—18–25 cm. in overall height, including flower canopy.
- *Plant width.*—20–25 cm. in width.
- *Plant hardiness.*—Hardy to minus 15° Centigrade.
- *Type.*—Perennial.
- *Root system.*—Fibrous.
- *Propagation.*—Propagation is accomplished using stem cuttings.
- *Cultural requirements.*—Plant in full sun, well-drained and moderately fertile soil and keep well fertilized and watered.
- *Diseases and pests.*—Susceptible to known *Dianthus* pests and disease but no other susceptibilities to pests or disease are known to the inventor.
- *Time required to produce a rooted cutting.*—5 weeks are needed to produce a rooted cutting.
- *Temperature recommended for cuttings to produce roots.*—The air temperature needed is a minimum of 15° Centigrade air temperature and base heat of 21° Centigrade.
- *Crop time.*—3–6 months is needed to produce a finished 1.5-liter container size from a well-rooted cutting.

Stem:
- *Shape.*—Cylindrical.
- *Stem dimensions.*—15–20 cm. in length and 2 mm. in diameter.
- *Stem surface.*—Glabrous and glaucous.
- *Stem color.*—122C.
- *Branching.*—Numerous basal breaks.
- *Internode length.*—15–55 mm. between nodes.
- *Node dimensions.*—3 mm. in diameter and 4 mm. in length.
- *Node color.*—122C.

Foliage:
- *Type.*—Evergreen.
- *Shape.*—Lanceolate.
- *Division.*—Simple.
- *Apex.*—Acute.
- *Base.*—Decurrent.
- *Venation.*—Not prominent.
- *Margins.*—Entire.
- *Attachment.*—Sheathing.
- *Arrangement.*—Opposite and spiraling up stem.
- *Surfaces* (*adaxial and abaxial*).—Glaucous.
- *Leaf dimensions.*—6–9 cm. in length and 3–5 mm. in width.
- *Leaf color* (*adaxial surfaces*).—122A.
- *Leaf color* (*abaxial surfaces*).—122A.
- *Stipules.*—Present.
- *Stipule dimensions.*—2 mm. in width and 8 mm. in length.
- *Stipule color.*—122A.
- *Fragrance.*—Absent.

Flowers:
- *Inflorescence.*—Raceme with branches.
- *Flower type.*—Double and symmetrical.
- *Flower shape.*—Salviform.
- *Flower dimensions* (*including calyx*).—40 mm. in length and 40–50 mm. in diameter.
- *Number of flowers per flower stem.*—From 2 to 5 flowers and buds per individual flowering stem.
- *Bud color.*—Each bud is 137A on apical half and 137B on basal half.
- *Anthocyanin.*—Absent.
- *Bud dimensions.*—18–20 mm. in length and 8–9 mm. in width.
- *Bud shape.*—Cylindrical.
- *Petals.*—Persistent, apopetalous, overlapping.
- *Petal number.*—20 petals in number.
- *Petal dimensions.*—38 mm. in length and 22 mm. in width.
- *Petal margin.*—Dentate (toothed 2–3 mm deep).
- *Petal shape.*—Obdeltoid.
- *Petal color* (*adaxial surface*).—Colors 69B, 60A and 145C are each individually present on each individual petal.
- *Petal color* (*abaxial surface*).—Colors 69C and 145C are each individually present on each individual petal.
- *Petal surfaces* (*adaxial and abaxial*).—Glabrous.
- *Calyx dimensions.*—8 mm. in width and 20 mm. in length.
- *Sepal color* (*adaxial surfaces*).—137A.
- *Sepal color* (*abaxial surfaces*).—138A.
- *Sepal apex.*—Acuminate.
- *Anthocyanin.*—Absent.
- *Sepal number.*—5 in number.
- *Fused or unfused.*—Fused.

*Epicalyx.*—4 bracts in number.
*Epicalyx dimensions* (*bracts*).—10 mm. in length and 7 mm. in diameter.
*Epicalyx color* (*adaxial surfaces*).—137A.
*Epicalyx color* (*abaxial surfaces*).—138A.
*Anthocyanin.*—Absent.
*Peduncle dimensions.*—20–90 cm. in length and 2–3 mm. in diameter.
*Peduncle surface.*—Glaucous.
*Peduncle color.*—122C.
*Fragrance.*—Strong perfume fragrance.
*Lastingness of flower.*—Each individual flower lasts 10 days at 20° Centigrade.

Reproductive organs:
*Stamens.*—Absent.
*Anther.*—Absent.
*Styles.*—Two in number.
*Style dimensions.*—18 mm. in length and 1 mm. in width.
*Style color.*—155A.
*Stigma.*—Single stigma.
*Color of stigma.*—155A.
*Stigma dimensions.*—5 mm. in length and 1 mm. in width.
*Pistils.*—2 in number.
*Pistil shape.*—Thread-like.
*Pistil color.*—155A.
*Ovary position.*—Superior.
*Ovary dimensions.*—6 mm. in length and 4 mm. in diameter.
*Ovary shape.*—Spindle shaped.
*Ovary color.*—145D.

Seed: 'Devon Yolande' does not set seed.

It is claimed:

1. A new and distinct cultivar of *Dianthus* plant named 'Devon Yolande' as described and illustrated herein.

* * * * *